(12) United States Patent
Hase et al.

(10) Patent No.: US 6,956,058 B2
(45) Date of Patent: Oct. 18, 2005

(54) METHOD FOR IMPROVING INSULIN RESISTANCE

(75) Inventors: Tadashi Hase, Tochigi (JP); Takatoshi Murase, Tochigi (JP); Hiroyuki Watanabe, Tochigi (JP); Hidehiko Kondo, Tochigi (JP)

(73) Assignee: Kao Corporation, Tokyo (JP)

(*) Notice: Subject to any disclaimer, the term of this patent is extended or adjusted under 35 U.S.C. 154(b) by 236 days.

(21) Appl. No.: 10/238,720

(22) Filed: Sep. 11, 2002

(65) Prior Publication Data

US 2003/0158257 A1 Aug. 21, 2003

Related U.S. Application Data

(63) Continuation-in-part of application No. 10/131,188, filed on Apr. 25, 2002.

(30) Foreign Application Priority Data

Apr. 26, 2001 (JP) .......................................... 2001-129847

(51) Int. Cl.⁷ ............................................. A61K 31/225
(52) U.S. Cl. ....................................... 514/547; 514/552
(58) Field of Search ................................ 514/549, 547, 514/552

(56) References Cited

U.S. PATENT DOCUMENTS

| | | | |
|---|---|---|---|
| 6,004,611 A | 12/1999 | Gotoh et al. ................. | 426/612 |
| 6,337,414 B1 | 1/2002 | Sugiura et al. .............. | 554/174 |
| 6,361,980 B2 | 3/2002 | Sugiura et al. .............. | 435/134 |
| 6,448,292 B2 | 9/2002 | Koike et al. ................. | 514/558 |
| 6,773,741 B1 | 8/2004 | Masui et al. ................. | 426/602 |

FOREIGN PATENT DOCUMENTS

| | | |
|---|---|---|
| FR | 2 599 382 | 5/1986 |
| JP | 62-132808 | 6/1987 |
| JP | 63-104917 | 5/1988 |
| JP | 64-2589 | 1/1989 |
| JP | 1-160988 | 5/1989 |
| JP | 1-174342 | 7/1989 |
| JP | 2-11516 | 1/1990 |
| JP | 2-45424 | 2/1990 |
| JP | 04-300825 | 10/1992 |
| JP | 04-300826 | 10/1992 |
| JP | 04-300828 | 10/1992 |
| JP | 08-214892 | 8/1996 |
| JP | 08-060181 | 3/1998 |
| JP | 10-057086 | 3/1998 |
| JP | 10-176181 | 6/1998 |
| JP | 10-265795 | 10/1998 |
| JP | 2001-64169 | 3/2001 |
| JP | 2001-064170 | 3/2001 |
| JP | 2001-064171 | 3/2001 |
| JP | 2001-064671 | 3/2001 |
| JP | 2001-064672 | 3/2001 |
| JP | 2001-098294 | 4/2001 |
| JP | 2001-247457 | 9/2001 |
| JP | 2001-247473 | 9/2001 |
| JP | 2001-302509 | 10/2001 |
| JP | 2002-003376 | 1/2002 |
| JP | 2002-138297 | 5/2002 |
| WO | WO99/48378 | 9/1999 |

OTHER PUBLICATIONS

Storlien et al., Lipids, 31/3, SUPPL. (S261–S265) (1996).*

Howell, S.L., Diabetologia, (Sep., 1994) 37 Suppl. 2 S30–5.*

Yukihisa Tanaka, et al, "Concentration of Docosahexaenoic Acid in Glyceride by Hydrolysis of Fish Oil with Candida cylindracea Lipase", J. Amerl. Oil Chem. Soc., vol. 69, No. 12, Dec. 1992.

Tamotsu Hoshino, et al, "Selective Hydrolysis of Fish Oil by Lipase to Concentrate n–3 Polyunsaturated Fatty Acids", Agric. Biol. Chem., 54 (6), p. 1459–1467, 1990.

Zu–Yi Li, et al, "Lipase–Catalyzed Esterification of Glycerol and n–3 Polyunsaturated Fatty Acid Concentrate in Organic Solvent", J. Ameri. Oil Chem. Soc., vol. 70, No. 8, Aug. 1993.

Bjornar Myrnes, et al, "Solvent–Free Enzymatic Glycerolysis of Marine Oils", J. Ameri. Oil Chem. Soc., vol. 72, No. 11, 1995.

Yuji Shimada, et al, "Selective Hydrolysis of Polyunsaturated Fatty Acid–Containing Oil with Geotrichum candidum Lipase", J. Ameri. Oil Chem. Soc., vol. 72, No. 12, p. 1577, 1995.

Harald Breivik, et al, "Preparation of Highly Purified Concentrates of Elcosapentaenoic Acid and Docosahexaenoic Acid", J. Ameri. Oil Chem. Soc., vol. 74, No. 11, p. 1425, 1997.

Stergios Moschos, M.D., et al, "Leptin and Reproduction: a Review", Fertility and Sterility, vol. 77, No. 3, pp. 433–444, Mar. 2002.

"Rinsho Kagaku (Clinical Science)", Vo. 34, pp. 1043–1048, 1998.

Daniel Ricquier, et al, "The Uncoupling Protein Homologues: UCP1, UCP2, UCP3, StUCP and AIUCP", Biochem J., vol. 345, pp. 161–179, 2000.

Takatoshi Murase, et al, "Abundant Expression of Uncoupling Protein–2 in the Small Intestine: Up–Regulation by Dietary Fish Oil and Fibrates", Biochimica et Biophysica Acta, vol. 1530, pp. 15–22, 2001.

(Continued)

*Primary Examiner*—Phyllis G. Spivack
(74) *Attorney, Agent, or Firm*—Oblon, Spivak, McClelland, Maier & Neustadt, P.C.

(57) ABSTRACT

Methods are disclosed for improving insulin resistance in a diabetic comprising administering a diacylglycerol.

3 Claims, 4 Drawing Sheets

OTHER PUBLICATIONS

Carmen Guerra, et al, "Abnormal Nonshivering Thermogenesis in Mice with Inherited Defects of Fatty Acid Oxidation", J. Clin. Inveset., vol. 102, No. 9, pp. 1724–1731, Nov. 1998.

World Intellectual Property Organization, WO 01/13733 A1, Mar. 1, 2001.

Kunio Yamamoto, et al, "Long–Term Ingestion of Dietary Diacylglycerol Lowers Serum Triacylglycerol in Type II Diabetic Patients with Hypertriglyceridemia", J. Nutri., vol. 131, p. 3204, 2001.

Takatoshi Murase, et al, "Dietary Diacylglycerol Suppresses High Fat and High Sucrose Diet–Induced Body Fat Accumulation in C57BL/6J Mice", Journal of Lipid Research, vol. 42, pp. 372–378, 2001.

Seikagaku (Biochemistry), vol. 70, pp. 212–216, 1998.

* cited by examiner

METHOD FOR IMPROVING INSULIN RESISTANCE

BACKGROUND OF THE INVENTION

This invention relates to a method for promoting accumulation of fatty acids into the small intestinal epithelium, and also to a method for improving lipid metabolism in the small intestine epithelium for the suppression of triacylglycerol synthesis, the enhancement of β-oxidation, the enhancement of uncoupling protein (UCP) expression, the promotion of energy consumption, the lowering of blood leptin level, the lowering of blood remnant level and/or the like purpose. This invention is also concerned with a method for treating diabetes and a method for improving lipid metabolism in a diabetic patient by ingesting diacylglycerol.

DESCRIPTION OF THE BACKGROUND

From research in recent years, elucidations have been made increasingly as to a connection between lipid metabolism disorders, such as an increase in blood leptin level and an increase in blood remnant level, and diseases such as angina pectoris, myocardial infarction, cerebral thrombosis, cerebral infarction and aortic aneurysm.

It is, therefore, desired to lower the remnant and leptin levels by improving lipid metabolism (Fertil Steril 2002 March; 77(3), 433–44).

Remnant-like lipoprotein particles (RLP; called "remnant particles" or simply "remnant") have been reported to be a strong risk factor for the above-described diseases, because they are susceptible to absorption into blood vessel walls and cholesterol in RLP so absorbed accumulates in the blood vessel walls. Leptin, which is a hormone secreted mainly from adipose tissues, on the other hand, has been reported to perform control on body fat and serum lipids by promoting energy consumption, through burning promoting effect for body fat. If lipid metabolism disorders continue, however, the serum leptin level increases and leptin can no longer exhibit its inherent effect. If this situation arises, it is necessary to lower the serum leptin level such that leptin can smoothly perform its function.

It is, therefore, very important for the prevention and treatment of diseases, which are associated with lipid metabolism, to lower blood remnant level and blood leptin level and also to promote energy consumption.

In general, lipids (triacylglycerols) ingested as a meal are degraded by lipase into fatty acids and 2-monoacylglycerol in the small intestine, and subsequently, most of the fatty acids and 2-monoacylglycerols are usually resynthesized into the triacylglycerols in the small intestine epithelium, followed by a move into blood. A portion of the fatty acids so formed, on the other hand, is subjected to catabolism in the small intestine epithelium and is converted into energy. In other words, the energy of the fatty acids is converted into an electrochemical potential of protons within mitochondria through a series of pathways such as β-oxidation and electron transport systems.

It is a function of an uncoupling protein (UCP) to uncouple oxidative phosphorylation. Described specifically, the electron transport system and ATP synthesis are closely coupled with each other by a proton gradient across mitochondrial inner membranes, and UCP is a special channel which eliminates this proton gradient in a short-cut manner. When UCP is activated, chemical energy of an oxidized substrate is converted into heat instead of being employed for ATP synthesis ("Seikagaku (Biochemistry)", 70, 212–216, 1998; "Rinsho Kagaku (Clinical Science)", 34, 1043–1048, 1998). Accordingly, a functional disorder of UCP and lowering in its expression are considered to decrease energy consumption and to lead to accumulation of energy and obesity. Conversely, an increase in the expression of UCP and its activation are considered to increase energy consumption and to result in anti-obesity.

It is also known that the small intestine is a tissue active in the expression of UCP, that the expression of small intestine UCP varies depending on dietary lipids, and that the expression of small intestine UCP is increased especially by fish oil having lipid metabolism improving effect. In view of these, small intestine UCP is suggested to play an important role in lipid metabolism (Biochem J., 345, 161–179, 2000; Biochimica et Biophysica Acta, 1530, 15–22, 2001).

The β-oxidation system is a principal metabolic degradation pathway for fatty acids. A group of enzymes, such as MCAD (medium-chain acyl-CoA dehydrogenase) and ACO (acyl-CoA oxidase), play parts in the β-oxidation pathway. The β-oxidation system plays an important role not only in the degradation of fatty acids but also in thermogenesis through conversion of fatty acids into energy. Deficit of β-oxidation enzyme has been reported to lead to a reduction in energy expenditure (J. Clin. Invest., 102, 1724–1731, 1998). Therefore, enhancement of β-oxidation is considered to improve lipid metabolism and energy metabolism and also to lead to an improvement in hyperleptinemia.

PPAR (peroxisome proliferator activated receptor) is a transcription factor which controls development of UCP and β-oxidation related molecules (acyl-CoA oxidase, medium chain acyl CoA dehydrogenase, etc.). Participation of fatty acids in the activation of PPAR is known well from experiments on cell level. As has been described above, oil (triacylglycerols) is generally degraded into 2-monoacylglycerols and fatty acids in the small intestinal tract, and subsequent to absorption, the 2-monoacylglycerols and fatty acids are resynthesized into triacylglycerols in the small intestine epithelium. The present inventors, therefore, postulated that, if it is possible to cause fatty acids to accumulate in the small intestine epithelium and to increase its concentration there, level/expression of β-oxidation related molecules and UCP would be increased. Under this postulation, the present inventors have proceeded with research. No specific method has been proposed yet to date for storing fatty acids in cells.

An object of the present invention is to provide a method for promoting accumulation of fatty acids into the small intestine epithelium. Another object of the present invention is to provide a method for improving lipid metabolism for the suppression of triacylglycerol synthesis, the enhancement of β-oxidation, the enhancement of uncoupling protein (UCP) expression, the promotion of energy consumption, the lowering of blood leptin level, the lowering of blood remnant level and/or the like purpose. A further object of the present invention is to provide a method for activating lipid catabolism in the small intestine.

Diacylglycerols are used for foods, as they have unique functions without side effects. Specifically, cholesterol level lowering agents (JP 63-104917 A), body weight gain suppressants (JP 4-300826 A), general-purpose oil compositions (U.S. Pat. No. 6,004,611), oil or fat compositions (WO 01/13733), vegetable-sterol-containing oil or fat compositions (WO 99/48378), body fat burning promoters (JP 2001-64672 A), and the like have been proposed.

Nonetheless, absolutely nothing is known as to what effects diacylglycerols exhibit in the small intestine.

In recent years, multiple risk factor syndrome called visceral fat syndrome, syndrome X or the death quartet, which is caused as a result of complication of certain factors such as obesity, hyperlipemia and hypertention in addition to diabetes, is attracting attention as a cause of cardiovascular disease. It has been reported that concerning diabetics, morbidity rate and mortality rate become higher upon onset of complications such as cardiovascular diseases. The onset rate of great vessel injuries (such as myocardial infarction) among diabetics is higher compared with that among those not suffering from diabetes. As causes of this tendency, the principal one is lipid metabolic disorder. For example, small dense LDL of the same particle size LDL cholesterol tends to occur in diabetics and acts as a cause of arteriosclerosis.

Further, type II diabetes which accounts for 90% or higher of diabetes is considered to be a state in which high blood sugar level has been developed by occurrence of reductions in the effects of insulin as a result of complication of a reduction in the secretion of insulin from the β cells of the pancreas and a reduction in insulin sensitivity (insulin resistance) at skeletal muscle, the liver and adipose tissue, which are insulin's target organs, to various extents. On the other hand, obesity caused by environmental factors such as binge eating, high fat diet and insufficient exercise is considered to take substantial part in insulin resistance together with genetic diathesis. The existence of obesity-associated insulin resistance leads, as its cost, to hyperinsulinemia. To insulin resistance caused by obesity, the body responds by excessively secreting insulin. When such a state (insulin resistance) continues, the cells of the pancreas exhaust so that the insulin secreting ability gradually drops to eventually result in diabetes conditions (high blood sugar). When this high blood sugar state continues, glucose itself increases secretion of insulin from the β cells of the pancreas and insulin resistance at peripheries, and hence, glucose toxicity is exhibited. A vicious circle is now formed, leading to further deteriorations in conditions.

Basic curing or treatment methods for diabetes are kinesiological therapy and dietary therapy. If the blood sugar level cannot be controlled by these methods alone, pharmacotherapy is then relied upon. It is important not only to control the blood sugar level but also to improve diabetes while taking complications into consideration. Accordingly, a pharmaceutical which can improve insulin resistance is believed to be extremely useful as a remedy for diabetes.

Another object of the present invention is, therefore, to provide a method for improving various factors of a diabetic, for example, sugar blood level, insulin resistance and lipid metabolic disorder.

SUMMARY OF THE INVENTION

The present inventor, therefore, conducted various investigations with a view to elucidating effects of diacylglycerols in the small intestine, especially in the small intestine epithelium. As a result, it has been found that diacylglycerols are degraded in the cavity of the small intestinal tract and subsequent to absorption in the small intestine epithelium, the resulting fatty acids are hardly reconstituted into triacylglycerols and accumulated there, and also that the thus-formed fatty acids induce the expression of genes involved in lipid metabolism in the small intestine and suppress synthesis of triacylglycerols. In other words, the present inventors have found that diacylglycerols have the lipid catabolism activating effect in the small intestine and lipid metabolism improving effect.

The present inventors also conducted further investigations on effects of diacylglycerols on diabetes model animals and the blood sugar level and insulin resistance in human, and effects of diacylglycerols on serum lipids in diabetics. As a result, it has been found that, when a diacylglycerol is ingested, the blood sugar level is lowered and the insulin resistance is improved. In addition, the ingestion of a diacylglycerol has also been found to reduce lipid metabolic disorders in a diabetic, for example, the serum triacylglycerol level, the concentration of triacylglycerols in VLDL fraction, the concentration of triacylglycerols in LDL fraction, and the concentration of triacylglycerols in small dense LDL fractions. Furthermore, the ingestion of a diacylglycerol has also been found to lower HOMA-R, which is an index of insulin resistance in a diabetic patient.

In one aspect of the present invention, there is thus provided a method for activating lipid catabolism in the small intestine epithelium, which comprises administering an effective amount of a diacylglycerol.

In another aspect of the present invention, there is also provided a method for promoting accumulation of fatty acids into the small intestine epithelium, which comprises administering an effective amount of a diacylglycerol.

In a further aspect of the present invention, there is also provided a method for inducing expression of a small intestine lipid metabolic gene, which comprises administering an effective amount of a diacylglycerol.

In a still further aspect of the present invention, there is also provided a method for suppressing synthesis of a triacylglycerol in the small intestine epithelium, which comprises administering an effective amount of a diacylglycerol.

In a still further aspect of the present invention, there is also provided a method for improving blood lipid metabolism, which comprises administering an effective amount of a diacylglycerol.

In a yet further aspect of the present invention, there is also provided a method for promoting energy consumption, which comprises administering an effective amount of a diacylglycerol.

In a yet further aspect of the present invention, there is also provided a method for treating diabetes, which comprises administering an effective amount of a diacylglycerol to a diabetic patient.

In a still yet further aspect of the present invention, there is also provided a method for improving lipid metabolism in a diabetic patient, which comprises administering an effective amount of a diacylglycerol to the diabetic.

In a still yet further aspect of the present invention, there is also provided a dietotherapeutic method for a diabetic patient, which comprises administering an effective amount of a diacylglycerol.

In a still yet further aspect of the present invention, there is also provided a medical food for a diabetic patient, which comprises a diacylglycerol.

In a still yet further aspect of the present invention, there is also provided a processed oil or fat food having insulin resistance improving effect, comprising a diacylglycerol.

Ingestion of diacylglycerols results in the accumulation of fatty acids in the small intestine. The fatty acids so accumulated promote induction of a β-oxidation enzyme to activate lipid catabolism at the small intestine, so that energy consumption is promoted and the fatty acids are hardly resynthesized into triacylglycerols. Further, ingestion of diacylglycerols over an extended time promotes burning of not only the diacylglycerols but also triacylglycerols ingested through other meals, and therefore, accumulation of body fat is suppressed. In addition, blood remnant-like lipoprotein and leptin levels are lowered, and lipid metabolism is improved.

Further, ingestion of a diacylglycerol by a diabetic leads not only to a reduction in blood sugar level and an improvement in insulin resistance but also to significant reductions in serum triacylglycerol level, the concentration of triacylglycerols in VLDL fraction, the concentration of triacylglycerols in small dense LDL fraction, the concentration of triacylglycerols in LDL fraction and the like so that lipid metabolism is improved.

DETAILED DESCRIPTION OF THE PREFERRED EMBODIMENTS

Constituent fatty acids of the diacylglycerol for use in the present invention may preferably be those having carbon numbers of from 8 to 24, especially from 16 to 22. Among the entire constituent fatty acids of the diacylglycerol, the content of unsaturated fatty acids may be preferably from 70 to 100 wt. % (hereinafter described simply as "%"), more preferably from 90 to 100%, particularly preferably from 93 to 100%, most preferably from 95 to 100%. From the standpoint of further enhancing the lipid metabolism improving effect, the fatty acid accumulation promoting effect and the diabetes treating effect, the (cis-form unsaturated)/(trans-form unsaturated+saturated) ratio may be preferably 6 or greater, more preferably from 9 to 25, still more preferably from 9 to 20. On the other hand, the particularly preferred content of the trans-form unsaturated fatty acids in the diacylglycerol may be 5% or lower and the especially preferred content of the saturated fatty acids may also be 5% or lower. From the standpoint of effects and oxidation stability, 15 to 90% of the constituent fatty acids comprise ω3 unsaturated fatty acids, with 20 to 80% being more preferred, 30 to 70% being still more preferred, and 40 to 65% being particularly preferred. Examples of the ω3 unsaturated fatty acids can include α-linolenic acid (C18:3), stearidonic acid (C18:4), eicosapentaenoic acid (C20:5), docosapentaenoic acid (C22:5) and docosahexaenoic acid (C22:6), with α-linolenic acid, eicosapentaenoic acid and docosahexaenoic acid being preferred, and α-linolenic acid being more preferred. Diacylglycerols include 1,3-diacylglycerols and 1,2-diacylglycerols (2,3-diacylglycerols). More preferably, the weight ratio of the 1,3-diacylglycerols to the 1,2-diacylglycerols may be 7:3.

From the standpoint of enhancing the lipid metabolism improving effect and the diabetes treating effect, increasing the accumulation of fatty acids and improving the industrial productivity, the 1,3-diacylglycerols may amount preferably to 50% or more, more preferably to 55 to 100%, especially to 60 to 90% of the whole diacylglycerols.

The diacylglycerol for use in the present invention can be produced, for example, by subjecting an oil or fat, which contains target constituent fatty acids, and glycerol to transesterification or by causing lipase to act on a mixture of the target constituent fatty acids or esters thereof and glycerol to conduct transesterification. From the standpoint of avoiding isomerization during the reaction, the transesterification making use of lipase is more preferred. In this transesterification making use of lipase, it is preferred, for the prevention of isomerization during a purification stage after completion of the reaction, to conduct the purification under such mild conditions that no isomerization of fatty acids would take place.

As is appreciated from the foregoing, it is preferred to use the diacylglycerol as an oil or fat composition which also contains triacylglycerols and the like. From the standpoint of effects, the oil or fat composition may contain preferably 15 to 100%, more preferably 40 to 99%, particularly preferably 60 to 95%, most preferably 80 to 95% of diacylglycerols. Fatty acids formed from diacylglycerols as a result of degradation by lipase in the course of digestion are more prone to accumulate in the small intestine epithelium than those formed from triacylglycerols. Use of an oil or fat composition containing 15% or more of diacylglycerols can, therefore, bring about excellent lipid metabolism improving effect. From the standpoint of the diabetes treating effect, it is also preferred to have diacylglycerols contained in a proportion of 15% or higher.

The oil or fat composition may contain triacylglycerols. From the standpoint of effects, taste and flavor, and oxidation stability, the content of the triacylglycerols in the oil or fat composition may range from 0 to 85%, preferably from 1 to 59.9%, more preferably from 5 to 39.9%, most preferably from 5 to 19.9%. As constituent fatty acids of the triacylglycerol, unsaturated fatty acids having the carbon numbers of which range from 16 to 22 may be contained preferably in a proportion of from 55 to 100%, more preferably in a proportion of from 70 to 100%, especially in a proportion of from 80 to 100%, most preferably in a proportion of from 90 to 97%, from the standpoint of effects, taste and flavor, and texture. From the standpoint of oxidation stability, ω3 unsaturated fatty acids may also be contained, as constituent fatty acids of triacylglycerols, preferably in a proportion of from 0 to 40%, more preferably in a proportion of from 0 to 30%, particularly in a proportion of from 0 to 20%, most preferably from 0 to 15%.

The oil or fat composition may also contain monoacylglycerols. From the standpoint of taste and flavor and oxidation stability, their content may be 0 to 30%, preferably 0.1 to 10%, more preferably 0.1 to 5%, especially preferably 0.1 to 2%, most preferably 0.1 to 1.5%. Constituent fatty acids of the monoacylglycerols may preferably the same as those of the diacylglycerols from the viewpoint of manufacture.

Free fatty acids contained in the oil or fat composition have an offensive taste and from the standpoint of taste, their content may be set below 10%, preferably below 5%, more preferably below 2.5%, especially preferably below 1%, most preferably below 0.5%.

Preferably, an antioxidant can be added to the oil or fat composition to improve its oxidation stability. Examples of the antioxidant can include butylhydroxyanisole (BHA), butylhydroxytoluene (BHT), vitamin A, vitamin C, vitamin E, phospholipids, polyphenol, and tert-butylhydroquinone (TBHQ). Two or more of these antioxidants can also be used in combination. The antioxidant may be contained preferably in a proportion of from 0.005 to 0.2%, especially in a proportion of from 0.04 to 0.1% in the oil or fat composition.

It is also preferred to further add a crystallization inhibitor to the oil or fat composition. Examples of crystallization inhibitors usable in the present invention can include polyol fatty acid esters such as polyglycerol condensed licinoleic acid esters, polyglycerol fatty acid esters, sucrose fatty acid esters, sorbitan fatty acid esters, polyoxyethylene sorbitan fatty acid esters and propylene glycol fatty acid esters. Two or more of these crystallization inhibitors can also be used in combination.

The crystallization inhibitor may be contained preferably in a proportion of from 0.02 to 0.5%, more preferably from 0.05 to 0.2% in the oil or fat composition.

In vegetable oil, phytosterols are contained in a proportion of from 0.05 to 1.2% or so. However, the content of phytosterols in an oil or fat composition differs depending on its production process. Use of a fatty acid, which is available abundantly on the market and was obtained by distillation, as a raw material, for example, results in an oil or fat composition in which the content of a phytosterol is low. In such a case, it is preferred to add phytosterols such that the oil or fat composition contains phytosterols in a total proportion of from 0.05 to 20%, especially from 0.3 to 1.2%. Examples of such phytosterols can include free forms such as α-sitosterol, β-sitosterol, stigmasterol, campesterol, α-sitostanol, β-sitostanol, stigmastanol and campestanol; and ester forms such as their fatty acid esters, ferulic acid esters and cinnamic acid esters.

In the methods according to the present invention, the diacylglycerol can be administered preferably at a daily dosage in a range of from 0.1 to 25 g, especially from 0.1 to 20 g per adult, generally once to several times in a day. Administration of 0.1 g/day in terms of the diacylglycerol is essential for the development of the effects.

When the methods according to the present invention are applied for the prevention or treatment of a disease, illustrative dosage forms can include oral preparations, for example, solid preparations such as powders, granules, capsules, pills and tablets, and liquid preparations such as solutions, suspensions and emulsions. These oral preparations can each be produced by adding, in addition to the above-described oil or fat composition, one or more of excipients, disintegrators, binders, lubricants, surfactants, alcohols, water, water-soluble polymers, sweeteners, corrigents, acidifiers, and the like, which are commonly employed depending on the forms of oral preparations. When the oil or fat composition is used, its content in each orally administered pharmaceutical may range generally from 0.05 to 100%, with 1 to 50% being particularly preferred, although the content varies depending on the application purpose and preparation form of the medicine.

To ingest diacylglycerols in the form of foods in the methods according to the present invention, processed oil or fat foods containing the diacylglycerols can be used. For example, diacylglycerols can be formulated into health foods, functional foods, foods for specified health use, medical foods or the like, which exhibit specific functions to promote health. Specific examples can include capsules, tablets and granules; bakery foods such as breads, cakes, cookies, pies, bar cookies and bakery mixes; salad dressings such as French dressing; oil-in-water emulsion foods such as mayonnaise; water-in-oil emulsion foods such as margarine and margarine-like spreads; confectioneries such as creams, chocolate and potato chips, ice cream and dessert; drinks; soups; sauces; coffee whitener; whipped cream; barbecue sauce; peanut butter; frying shortening; baking shortening; processed meat products; frozen foods; powdered foods; meal replacers; and food materials such as cooking oils useful for tempura, fries and frizzled dishes. These foods can each be produced by adding, in addition to an oil or fat composition, one or more food materials commonly employed depending on the kind of the food. The content of the oil or fat composition in each of these foods may range generally from 0.05 to 100%, particularly preferably from 0.5 to 80%, although it differs depending on the kind of the food.

A description will hereinafter be made about processed oil or fat foods according to the present invention, each of which contains a diacylglycerol. The term "processed oil or fat food" as used herein means a food obtained by mixing an oil or fat composition, which contains 15% or more of a diacylglycerol, with one or more other food materials or ingredients and then processing the resulting mixture. Food raw materials or ingredients usable in such processed oil or fat foods can include:

(1) Edible oils or fats

No particular limitation is imposed on an edible oil or fat for use in the present invention insofar as it is a common edible oil or fat. Examples can include natural, animal or vegetable oils or fats and processed oils or fats obtained by subjecting them to ester interchange, hydrogenation, fractionation or the like. Preferred usable examples can include vegetable oils such as soybean oil, rapeseed oil, cottonseed oil, rice bran oil, corn oil, sunflower oil, palm oil, palm karnel oil and coconut oil; and their processed oils and fats.

(2) Emulsifiers

No particular limitation is imposed on emulsifiers in so far as they are commonly used in foods. Illustrative are sugar fatty acid esters, sorbitol fatty acid esters, glycerol fatty acid esters, lecithin and degradation products thereof, egg proteins, soybean proteins, milk proteins, and various proteins, peptides and the like obtained from these proteins by isolation or hydrolysis.

(3) Thickeners

No particular limitations are imposed on thickeners in so far as they are commonly used in foods. Illustrative are polysaccharides such as xanthan gum, gellan gum, guar gum carageenan, pectin, tragacanth gum and various starches; and proteins such as gelatin and proteins.

(4) Various tasting agents such as common salt, sugar, vinegar, and Seasonings (5) Various condiments such as spices and flavors (6) Various food coloring matters (7) Antioxidants such as tocopherol and natural antioxidant ingredients Preferred illustrative formulas will hereinafter be described. It should, however, be borne in mind that they by no means limit use of the present invention.

a) Acidic Oil-in-Water Type Oil or Fat Processed Foods

Oil phase/water phase: 20/80 to 80/20 (preferably 30/70 to 70/30).

Amount of diacylglycerol: 15% or higher based on the oil or fat in an oil phase (preferably 40% or more, notably 80% or more).

Amount of phytosterol: 0.05% or more based on the oil or fat in an oil phase.

Amount of emulsifier: 0.05 to 5%.

pH: 2 to 6.

The pH is adjusted with vinegar, an organic acid such as citric acid or a salt thereof, or an acidifier such as lemon juice. Using the above-described raw materials or ingredients, acidic oil-in-water type oil or fat processed foods such as salad dressings and mayonnaise, which have insulin resistance improving effect and diabetes improving effect, can be prepared by methods known per se in the art.

| <Illustrative formula> Mayonnaise | |
|---|---|
| | Parts by weight |
| Water phase | |
| Common salt | 3.0 |
| Sugar | 1.0 |
| Seasoning (sodium glutamate) | 0.5 |
| Spice (mustard powder) | 0.3 |
| Egg yolk | 14 |
| Vinegar (acidity: 10%) | 8 |
| Thickener | 0.5 |
| Water | 22.7 |
| Oil phase | |
| Oil composition I | 50 | b) Plastic Water-in-Oil Type Oil or Fat Processed Foods

Water phase/oil phase: 15/85 to 85/15 (preferably 20/80 to 50/50).

Amount of phytosterol: 15% or more (preferably 40% or more, notably 50% or more) based on the oil or fat in an oil phase.

Amount of phytosterol: 0.05% or more based on the oil or fat in an oil phase.

Using the above-described materials or ingredients, plastic water-in-oil type oil or fat processed foods such as margarine and margarine-like spreads, which have insulin resistance improving effect and diabetes improving effect, can be prepared by methods known per se in the art.

| <Illustrative formula> Margarine-like spread | |
|---|---|
| | Parts by weight |
| Oil phase | |
| Oil or fat* | 69.3 |
| Lecithin | 0.1 |
| Monoacylglycerol | 0.5 |
| Flavor | 0.1 |
| Water phase | |
| Water | 28.4 |
| Skim milk | 0.3 |
| Common salt | 1.3 |

*Oil composition I - 70% partially hydrogenated palm oil (IV = 40): 30% (melting point: 36° C.).

c) Bakery Foods

Amount of oil or fat: 10 to 40%.

Amount of diacylglycerol: 15% or more (preferably 40% or more, notably 50% or more) based on the amount of the oil or fat in an oil phase.

Amount of phytosterol: 0.05% or more based on the the amount of the oil or fat in the oil phase.

Wheat flour: 20 to 65%.

Sugar: 5 to 30%

Whole egg: 0 to 20%

Common salt: 0.1 to 2%

Baking powder. 0 to 1%

Using the above-described raw materials or ingredients, bakery foods such as shortbread (bar cookies) and brioche, which have insulin resistance improving effect and diabetes improving effect, can be prepared by methods known per se in the art.

| <Illustrative formula> Shortbread (bar cookies) | |
|---|---|
| | Parts by weight |
| Wheat flour | 60 |
| Oil composition I | 10 |
| Sugar | 24.6 |
| Common salt | 0.4 |
| Whole egg | 5 |

Administration of diacylglycerols or an oil or fat composition with diacylglycerols contained therein accelerates the accumulation of fatty acids in the small intestine epithelium. Further, the expression of the gene of β-oxidation enzymes and the gene of UCP, each of which takes part in the metabolism of lipids in the small intestine, is promoted. Furthermore, the synthesis of triacylglycerols in the small intestine epithelium is suppressed.

By these effects for promoting the accumulation of fatty acids in the small intestine epithelium and activating lipid catabolism, energy consumption is enhanced. Further, continued ingestion of diacylglycerol or an oil or fat composition with diacylglycerol contained therein facilitates burning not only of the diacylglycerol itself but also of lipids ingested as meals and also suppresses their accumulation as body fat.

In addition, as a result of activation of lipid metabolism in the small intestine epithelium by the methods of the present invention, PLLP-C, which is determined by quantitating blood RLP with cholesterol (Nakajima, K., Clin. Chim. Acta, 223, 53–71, 1993), and blood leptin level are lowered.

Further, ingestion of diacylglycerols or an oil or fat composition with diacylglycerols contained therein by a diabetic patient, especially a type II diabetic patient leads to a reduction in blood sugar level and an improvement in insulin resistance. In particular, HOMA-R, an index of insulin resistance, drops significantly. Moreover, ingestion of diacylglycerols or an oil or fat composition with diacylglycerols contained therein by a diabetic patient, especially a type II diabetic patient also leads reductions in serum triacylglycerol level and in the concentrations of triacylglycerols in lipoprotein fractions such as VLDL, LDL and small dense LDL.

The amount of diacylglycerols to be ingested by a diabetic patient may be in a range of from 0.1 to 25 g, especially from 0.1 to 20 g per adult. It is preferred to divide this amount into 1 to several portions in a day. The period of ingestion may be at least 1 week, preferably at least 2 weeks, more preferably at least 3 weeks, still more preferably at least 1 month, especially at least 2 months, most preferably at least 3 months. To allow a diabetic patient to ingest diacylglycerols for such a long period as described above, it is preferred to prepare medical foods for diabetes, in each of which diacylglycerols are used in place of a portion or the entire portion of triacylglycerols, and to allow him or her to ingest them.

EXAMPLES

Examples will hereinafter be described. It is, however, to be borne in mind that the present invention shall not be limited the following Examples.

The following oil compositions were prepared in accordance with the below-described procedure.

Oil or Fat Composition A

Fatty acids, which had been obtained by hydrolyzing commercial soybean oil the trans acid content of which was 0.8%, were subjected to wintering to lower the content of saturated fatty acids. Using commercial immobilized 1,3-position-selective lipase ("Lipozyme 3A", trade name; product of Novo-Nordisk Industries A.S.) as a catalyst, those fatty acids and glycerol were subjected to esterification at 40° C. After the lipase preparation was filtered off, the reactant was purified by molecular distillation to obtain an oil or fat composition A.

Oil or Fat Composition B

Fatty acids, which had been obtained by hydrolyzing commercial rapeseed oil the trans acid content of which was 0.6%, and glycerol were subjected to esterification at 40° C. by using "Lipozyme 3A". After the lipase preparation was filtered off, the reactant was purified by molecular distillation to obtain an oil or fat composition B.

Oil or Fat Composition C

Fatty acids, which had been obtained by hydrolyzing commercial rapeseed oil the trans acid content of which was 2.8%, and glycerol were subjected to esterification at 40° C. by using "Lipozyme 3A". After the lipase preparation was filtered off, the reactant was purified by molecular distillation to obtain an oil or fat composition C.

Oil or Fat Composition D

Commercial high docosahexaenoic acid oil and glycerol were mixed together, and subjected to transesterification at 100° C. under reduced pressure by using an alkali catalyst (sodium methoxide). After the catalyst was filtered off, the reactant was purified by molecular distillation to obtain an oil or fat composition D.

Oil or Fat Composition E

Linseed oil fatty acids and glycerol were subjected to esterification at 40° C. by using "Lipozyme IM" (trade name; product of Novo-Nordisk Industries A.S.). After the lipase preparation was filtered off, molecular distillation was conducted at 215° C. Subsequent to water washing, deodorization was performed at 215° C. for 2 hours to obtain an oil or fat composition E.

The acylglycerol compositions and diacylglycerol-constituent fatty acid compositions of the thus-produced oil or fat compositions (A–E) and soybean oil were analyzed by the below-described methods. The results are shown in Tables 1 and 2.

[Determination of the Acylglycerol Compositions]

Each oil was trimethyl silylated with a silylating agent ("Silylating Agent TH" trade name; product of Kanto Kagaku K. K.), and using a capillary column ("DBTM-1", trade name; product of J & W Scientific Inc.), the trimethyl silylated oil was then analyzed by gas chromatography.

[Determination of the Diacylglycerol-Constituent Fatty Acid]Compositions

Diacylglycerol fractions in each oil were collected by column chromatography [after triacylglycerol fractions had been eluted using "Wako Gel C-200", trade name; product of Wako Pure Chemical Industries, Ltd.) and hexane, the diacylglycerol fractions were obtained with a 70:30 mixed solvent of hexane and ethyl ether]. Subsequent to methyl esterification by a method known per se in the art, an analysis was performed by gas chromatography equipped with a capillary column ("CP-SIL88", trade name; product of Chrompack Inc.).

TABLE 1

Acylglycerol Compositions (%)

| Oil or fat composition | Monoacyl-glycerols | Diacylglycerols (% of 1,3-DG) | Triacyl-glycerols | Phyto-sterols |
|---|---|---|---|---|
| A | 1.1 | 85.7 (59.9) | 12.7 | 0.5 |
| B | 0.9 | 85.0 (59.5) | 13.2 | 0.9 |
| C | 1.5 | 80.8 (56.5) | 16.7 | 1.0 |
| D | 0.9 | 53.1 (37.0) | 45.8 | 0.2 |
| E | 1.0 | 84.8 (59.3) | 14.0 | 0.2 |
| Soybean oil | ND | 1.0 | 98.7 | 0.3 |

ND: Not detected

TABLE 2

Fatty Acid Compositions (%)

| | Oil or fat composition | | | | | Commercial |
|---|---|---|---|---|---|---|
| Constituent fatty acids | A | B | C | D | E | soybean oil |
| C14 | — | — | — | 1.6 | — | — |
| C16 | 1.3 | 3.8 | 4.2 | 9.3 | 5.3 | 10.8 |
| C16:1 | — | — | — | 3.4 | — | — |
| C18 | 1.2 | 2.8 | 1.7 | 2.7 | 3.3 | 4.2 |
| C18:1 | 26.9 | 65.2 | 58.0 | 11.0 | 18.7 | 24.4 |
| Cis | 26.9 | 65.2 | 56.3 | NT | 18.7 | 24.4 |
| Trans | 0.0 | 0.0 | 1.7 | NT | — | 0.0 |
| C18:2 | 60.7 | 17.8 | 24.3 | 1.4 | 15.4 | 51.6 |
| Cis | 59.7 | 17.4 | 21.0 | NT | 15.4 | 51.3 |
| Trans | 1.0 | 0.4 | 3.3 | NT | — | 0.3 |
| C18:3 | 7.8 | 9.0 | 8.7 | 0.7 | 55.2 | 7.2 |
| Cis | 6.6 | 6.7 | 7.1 | NT | 52.8 | 6.7 |
| Trans | 1.2 | 1.2 | 1.6 | NT | 2.4 | 0.5 |
| C20 | 0.0 | 0.5 | 1.2 | — | — | 0.4 |
| C20:1 | — | — | — | 1.6 | — | — |
| C20:5 | — | — | — | 6.6 | — | — |
| C22:1 | — | — | — | 1.1 | — | — |
| C22:6 | — | — | — | 45.7 | — | — |
| Uk | 1.0 | 2.0 | 1.9 | 14.9 | 0.8 | 1.4 |
| Trans | 2.2 | 1.6 | 6.6 | NT | 2.4 | 0.8 |
| Saturated | 2.5 | 7.1 | 7.1 | 13.6 | 8.6 | 15.4 |
| Trans + saturated | 4.7 | 8.7 | 13.7 | — | 11.0 | 16.2 |
| Cis | 94.3 | 89.3 | 84.4 | — | 86.9 | 82.4 |
| Cis/(trans + saturated) | 20.1 | 11.3 | 6.2 | NT | 7.9 | 5.1 |

Uk: Unknown component,
NT: Not tested.

Example 1

Small Intestine Perfusion Test

The following test was conducted in accordance with the method described in J. Lipid Res., 39, 963 (1998).

Under anesthesia, Wistar rats (male, 6 weeks old) were each incised at the abdomen, and a cannula ("PE50", trade name; product of Clay Adams, Inc.) was arranged right underneath the pylorus. By a restraint gauge, an emulsion of triacylglycerols or diacylglycerols (triacylglycerols of diacylglycerols calculated as fatty acids: 90 mM, sodium chloride: 0.15 M, 10 mM tris-HCl buffer: q.s. to pH 7.0, taurocholic acid: 10 mM) was perfused at a rate of 4.5 mL/hr (Experiment 1). Five hours later, the perfusing was stopped, and 1 mL of RI-labeled fatty acids was promptly injected together with the emulsion of triacylglycerols or diacylglycerols (Experiment2). Namely, Experiment 1 was conducted such that the final concentration of [carboxy-$^{14}$C]TO (triolein) or 1,3-[carboxy-$^{14}$C]DO (diolein) reached $3.2 \times 10^6$ dpm/mL, while Experiment 2 was conducted such that the final concentration of [1-$^{14}$C]linoleic acid reached 1.6×10$^6$ dpm/mL. Subsequently, the above-described emulsion of triacylglycerols or diacylglycerols was injected again at the rate of 4.5 mL/hr. Five minutes later, Nembutal was injected into the abdominal cavity, the small intestine (40 cm from the pylorus) was sampled and placed in ice-cold 0.15 M sodium chloride. It took 5 minutes from the completion of the injection of the labeled substance until the sampling of the small intestine in the ice-cold saline. After the small intestine was cut into four equal parts and were then opened, the small intestine was washed with 0.15 M sodium chloride (once), 0.2% Triton-X100 (once), and 0.15 M sodium chloride (twice). The mucosa of the small intestine was scraped off and homogenized by a glass/Teflon® homogenizer in 0.15 M sodium chloride (10 mL). From 1 mL of the mucosa homogenate, lipids were extracted by the Folch partition method. The thus-obtained lipids were developed on a TLC plate (hexane:diethyl ether:acetic acid=80:20:1 (v/v/v, chloroform:acetone=96:4 (v/v), and measurements were conducted to determine the quantities of the label absorbed in FFA, 1,3-diacylglycerols, 1,2-diacylglycerols and triacylglycerols, respectively. The test results are shown in Table 3.

TABLE 3

|  | Triacylglycerols | Diacylglycerols | Significant test |
|---|---|---|---|
| Free fatty acids | 100 | 182 | <0.05 |
| 1,3-Diacylglycerols | 100 | 400 | <0.001 |
| 1,2-Diacylglycerols | 100 | 106 | — |
| Triacylglycerols | 100 | 94 | <0.001 |

Shown in terms of relative value when the amounts of the fatty acids and respective acylglycerols existed during the perfusing of triacylglycerols were each supposed to be 100.

When the diacylglycerols were perfused, the amounts of free acids and 1,3-diacylglycerols existed in the mucosa of the small intestine epithelium were significantly high compared with the corresponding amounts when the triacylglycerols were perfused. On the other hand, no significant difference was observed in the amount of the 1,2-diacylglycerol. In the diacylglycerol-administered group, the amount of triacylglycerols occurred as a result of re-synthesis in the small intestine epithelium was significantly loser compared with that in the triacylglycerol administration group.

Example 2

Induction of Small Intestine Lipid Metabolic Gene Expression by the Ingestion of Diacylglycerols Wistar rats (male, 7 weeks old) were each fed with an experimental feed with 20% of a diacylglycerol-containing oil composition or soybean oil contained therein and reared for 7 days. On the last day, those rats were each dissected to sample the tissue of the small intestine. From the tissue of the small intestine, RNA was isolated, and by Northern blotting, the expressed quantity of a lipid metabolism associated (β-oxidation) enzyme (MCAD: medium-chain acyl-CoA dehydrogenase) mRNA was analyzed. The results are shown in Table 4.

TABLE 4

|  | Soybean oil | Oil or fat composition B | Oil or fat composition E |
|---|---|---|---|
| MCAD mRNA | 100 | 130 | 145 |

Shown in terms of relative value when the expressed quantity of the MCAD mRNA in the case of soybeans was supposed to be 100.

By the ingestion of the diacylglycerol-containing oil or fat compositions B or E, the expression of the small intestine lipid metabolic gene was promoted, and lipid metabolism was enhanced. Further, the diacylglycerol containing α-linolenic acid as a main constituent fatty acid activated the lipid metabolism system more strongly than the diacylglycerol containing linoleic acid or oleic acid as a main constituent fatty acid.

Example 3

Inhibition Test of Triacylglycerol Synthesis in the Small Intestine Epithelium

Using FCS(fetal calf serum)-free, Dulbecco's modified Eagle's medium (D-MEM) with 5% FBS and 70 μg/mL kanamycin added therein, a rat small-intestine epithelial cell strain, IEC-6, was incubated under 5% $CO_2$ at 37° C. Individual fatty acids (oleic acid, linoleic acid, γ-linolenic acid, arachidonic acid, α-linolenic acid, eicosapentaenoic acid, and docosahexaenoic acid) were formed into complexes with 250 μM fatty-acid-free bovine serum albumin, and were added at a concentration of 200 μM, respectively. Twenty-four hours later, the individual cultures were washed with PBS and subsequent to treatment with tripsin, were peeled off from Culture dishes. Those cultures were separately suspended in portions of HBSS which contained Nile Red (100 ng/mL). Subsequent to incubation at room temperature for 5 minutes or longer, FACS analysis was conducted. From average fluorescence intensities, synthesized quantities of triacylglycerols were measured. The results are shown in Table 5.

TABLE 5

| Fatty acid |  | Fluorescence intensity |
|---|---|---|
| Linoleic acid | ω 6 | 100 |
| γ-Linolenic acid |  | 70 |
| Arachidonic acid |  | 87 |
| Oleic acid | ω 9 | 191 |
| α-Linolenic acid | ω 3 | 42 |
| Eicosapentaenoic acid |  | 52 |
| Docosahexaenoic acid |  | 49 |

Relative values of average fluorescence intensities when the average fluorescence intensity of linoleic acid was supposed to be 100.

As a result, among these fatty acids, those most hardly synthesized into triacylglycerols were the ω3 fatty acids (α-linolenic acid, eicosapentaenoic acid and docosahexaenoic acid), followed by the (ω6fatty acids (linoleic acid, γ-linolenic acid and arachidonic acid). The ω9 fatty acid (oleic acid) was most liable to synthesis into the corresponding triacylglycerol among these fatty acids.

It has been found that a difference arises in the amount of synthesized triacylglycerols depending on the kinds of fatty acids which exist in the epithelial cells of the small intestine.

Example 4

Effect of Diacylglycerols on Energy Metabolism

Male rats of an SD strain (7 weeks old) (Japan Charles River Inc.) were provided, and they were provisionally reared for 3 days. Using a 10% diacylglycerol (DAG) added feed (DAG group: n=6) or a 10% triacylglycerol (TAG) added feed (TAG group: n=7), they were then subjected for 1 week to two-meals-a-day rearing (eating time: 8:00 to 9:00; 21:00 to 22:00) in which the feed was given twice a day. With respect to the rats which had learned the timing of feed ingestion as described above, an expiration analysis was conducted for 22 hours (19:00 to 17:00) Using "Oxymax v. 5. 61" (trade name; manufactured by Columbus Instruments), the expiration analysis was conducted to measure the volume of oxygen consumed by the rats and the volume of carbon dioxide excreted by the rats.

TABLE 6

Compositions of Rat Feeds

|  | TAG feed group (%) | DAG feed group (%) |
| --- | --- | --- |
| TAG | 10 | 0 |
| DAG | 0 | 10 |
| Casein | 20 | 20 |
| Cellulose | 8.1 | 8.1 |
| Mineral mix | 4 | 4 |
| Vitamin mix | 2.2 | 2.2 |
| Potato starch | 55.5 | 55.5 |
| L-methionine | 0.2 | 0.2 |
| Total | 100.0 | 100.0 |

DAG: Oil or fat composition B
TAG: Soybean oil

Figure 1:
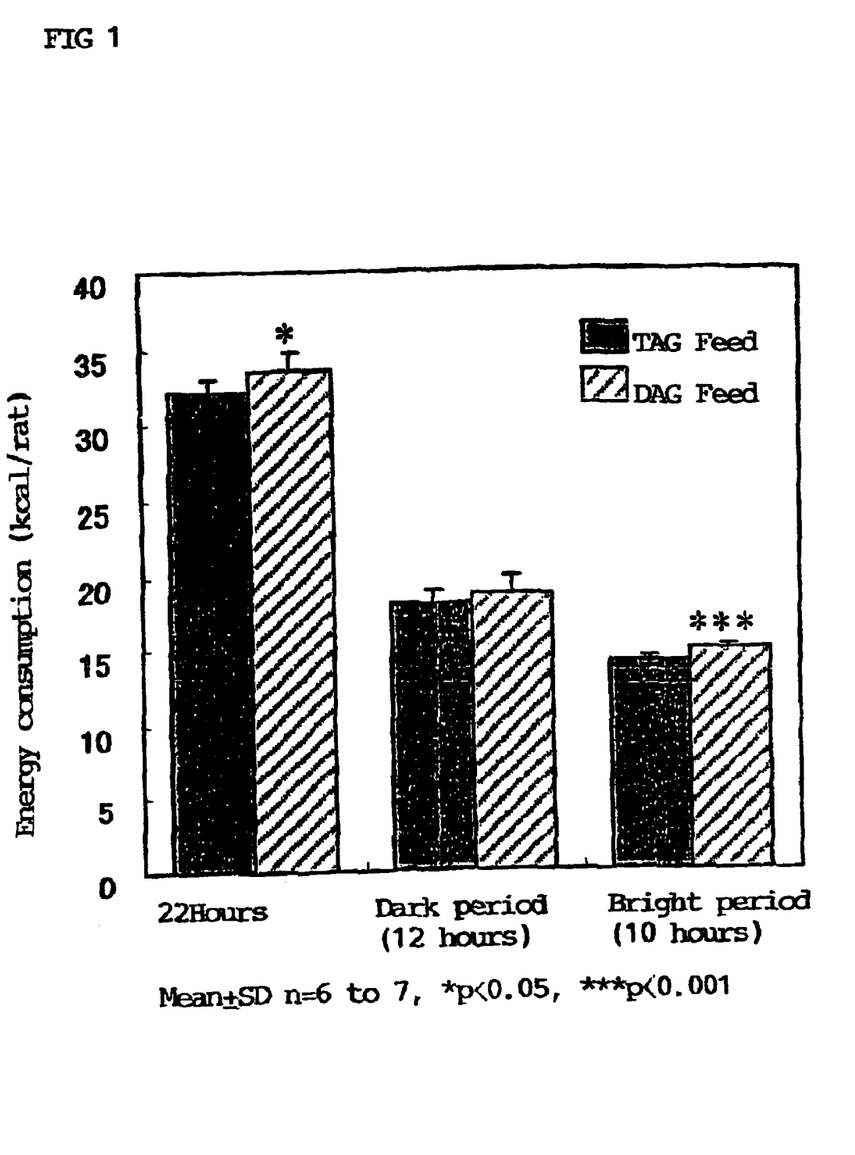
FIG. 1 shows variations in energy consumptions by rats, which ingested diacylglycerols (DAG) and triacylglycerols (TAG), respectively, in 22 hours.

As a result, the DAG group was significantly high in the total energy consumption over 22 hours than the TAG group ($p<0.05$ vs the TAG group) although there was no difference between the DAG group and the TAG group in the amount of the ingested feed during the 1-week pre-rearing and the measurement of the energy metabolism volumes (22 hours). Especially in an inactive, bright period (7:00 to 17:00), the total energy consumption significantly increased ($p<0.001$ vs the TAG group) (FIG. 1). As the ingestion of diacylglycerols led to higher energy consumption than that of triacylglycerols, it was suggested that diacylglycerols are more easily burnable as energy. Diet (meal) induced thermogenesis (DIT) was enhanced especially after the ingestion of diacylglycerols.

Example 5

Effect of Diacylglycerols on the Burning of Dietary Lipids

Subsequent to rearing for 4 weeks with a feed which contained diacylglycerols (DAG) at a concentration of 30% (Table 7), mice (CLEA Japan, Inc.) (n=8 per group) were fasted for 14 hours. Subsequently, triacylglycerols (TAG) which contained 28% of tripalmitin labeled with $^{13}C$ at the 1-position thereof were administered as an emulsion, the composition of which is shown in Table 8, once by using a feeding tube ("Safeed Fr.3.5", trade name; product of Terumo Corporation). As a control, mice (n=8) which had been reared for 4 weeks with a feed containing 30% of TAG of the same fatty acid composition were fasted and administered likewise. After the administration of the emulsion, the mice in the respective groups were separately placed in metabolic cages ["METABOLICA" (trade mark), manufactured by Sugiyama-Genki Iriki Co., Ltd.)], and their expirations were caused to be absorbed in portions of a 5 N aqueous solution of sodium hydroxide before the initiation of the experiment and from the $0^{th}$ hour to $10^{th}$ hour, from the $10^{th}$ hour to $24^{th}$ hour and from the $24^{th}$ hour to $33^{rd}$ hours, all after the administration of the emulsion. During the 33 hours for the sampling of the expirations, the DAG feed (the TAG feed for the control) and drink water were given ad libitum. The $CO_2$ in each expiration sample, which was collected in the aqueous sodium hydroxide solution, was caused to precipitate as $CaCO_3$ by using calcium chloride and ammonium chloride. The amount of $^{13}C$ contained in the $CaCO_3$ was determined using a mass spectrometer ("ANCA-SL", trade name; manufactured by PDZ Europe Ltd.). In this manner, variations in the level of $^{13}C$—$CO_2$ in the expiration from the mice in each group were investigated. Further, mice were similarly reared, and were likewise orally administered with triacylglycerols which contained [1-$^{13}C$]-tripalmitin labeled with $^{13}C$ at the 1-position thereof. Those mice were then fed with the same test feeds, respectively, and were sacrificed 24 hours later or 32 hours later to collect their epididymal fat tissues and mesenteric fat tissues. From each of those organs, lipids were extracted with a 1:2 v/v mixed solvent of methanol and chloroform. The amount of $^{13}C$ in the whole lipids was quantitated, and was presented as a percent accumulation based on the administered amount.

TABLE 7

Compositions of Mouse Feeds

|  | TAG feed group (%) | DAG feed group (%) |
| --- | --- | --- |
| TAG | 30 | 0 |
| DAG | 0 | 30 |
| Sucrose | 13 | 13 |
| Cellulose | 4 | 4 |
| Mineral mix | 3.5 | 3.5 |
| Vitamin mix | 1 | 1 |
| Potato starch | 48.5 | 48.5 |
| Total | 100.0 | 100.0 |

DAG: Oil or fat composition B,
TAG: Soybean oil

TABLE 8

Composition of emulsion

|  | (%) |
| --- | --- |
| Mixed lipids | 5 |
| Lecithin | 0.2 |
| Albumin | 2 |
| Distilled water | 92.8 |
| Total | 100.0 |

Mixed lipids (with 28% of $^{13}C$-labeled tripalmitin)

Figure 2:
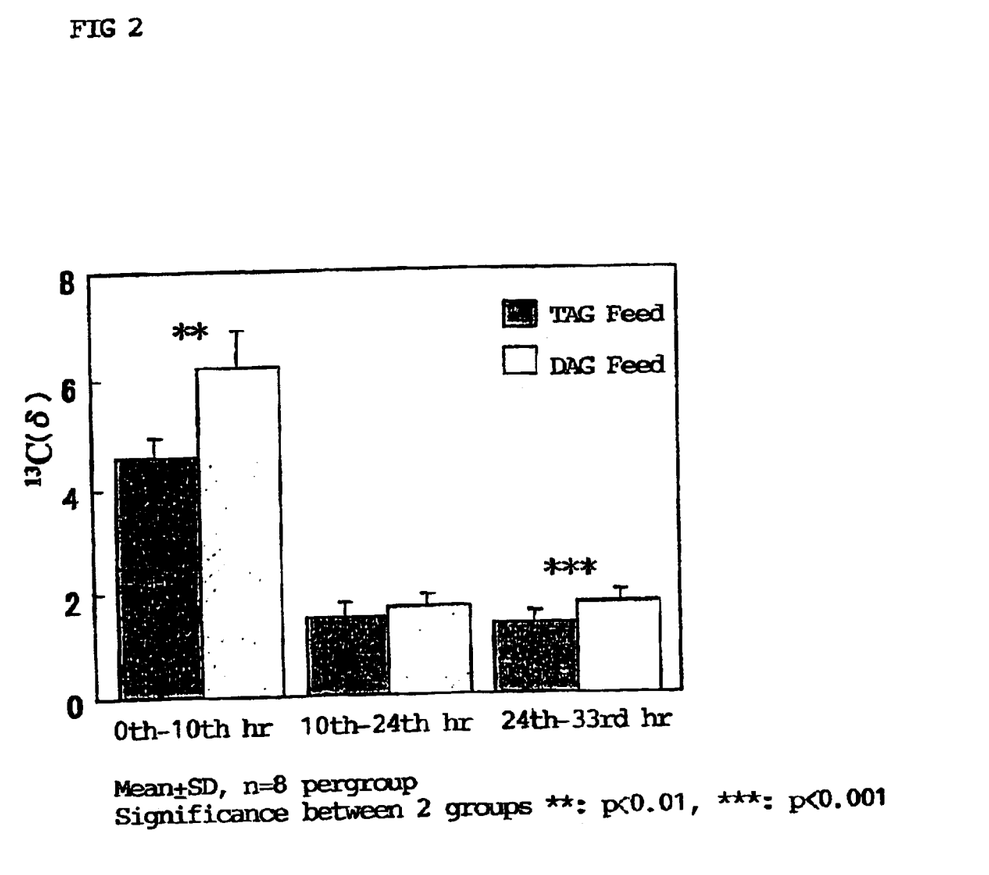
FIG. 2 illustrates variations in the concentrations of $^{13}C$—$CO_2$ in expirations from mice, which ingested diacylglycerols (DAG) and triacylglycerols (TAG), respectively, after administration of $^{13}C$-tripalmitin.

As a result, in each of the DAG administered group and the control group, $^{13}C$—$CO_2$ derived from the single-administered lipids was released into the expiration from the $0^{th}$ hour to $10^{th}$ hour after the administration of the labeled lipids, and after the $10^{th}$ hour, its concentration dropped (FIG. 2). Further, the amounts of $^{13}C$—$CO_2$ in the expirations from the $0^{th}$ hour to $10^{th}$ hour and from the $24^{th}$ hour to $33^{rd}$ hour were significantly higher in the TAG feed group than in the DAG feed group although there was no difference in the amount ingested during the expiration sampling time between the DAG group and the TAG group. This clearly indicates that long-term ingestion of diacylglycerols promotes oxidative degradation (burning) of TAG ingested from other feeds. As body fat accumulation suppressing effect of diacylglycerols, energy releasing effect associated with burning of dietary lipids subsequent to ingestion of diacylglycerols was demonstrated.

Figures 3A, 3B:
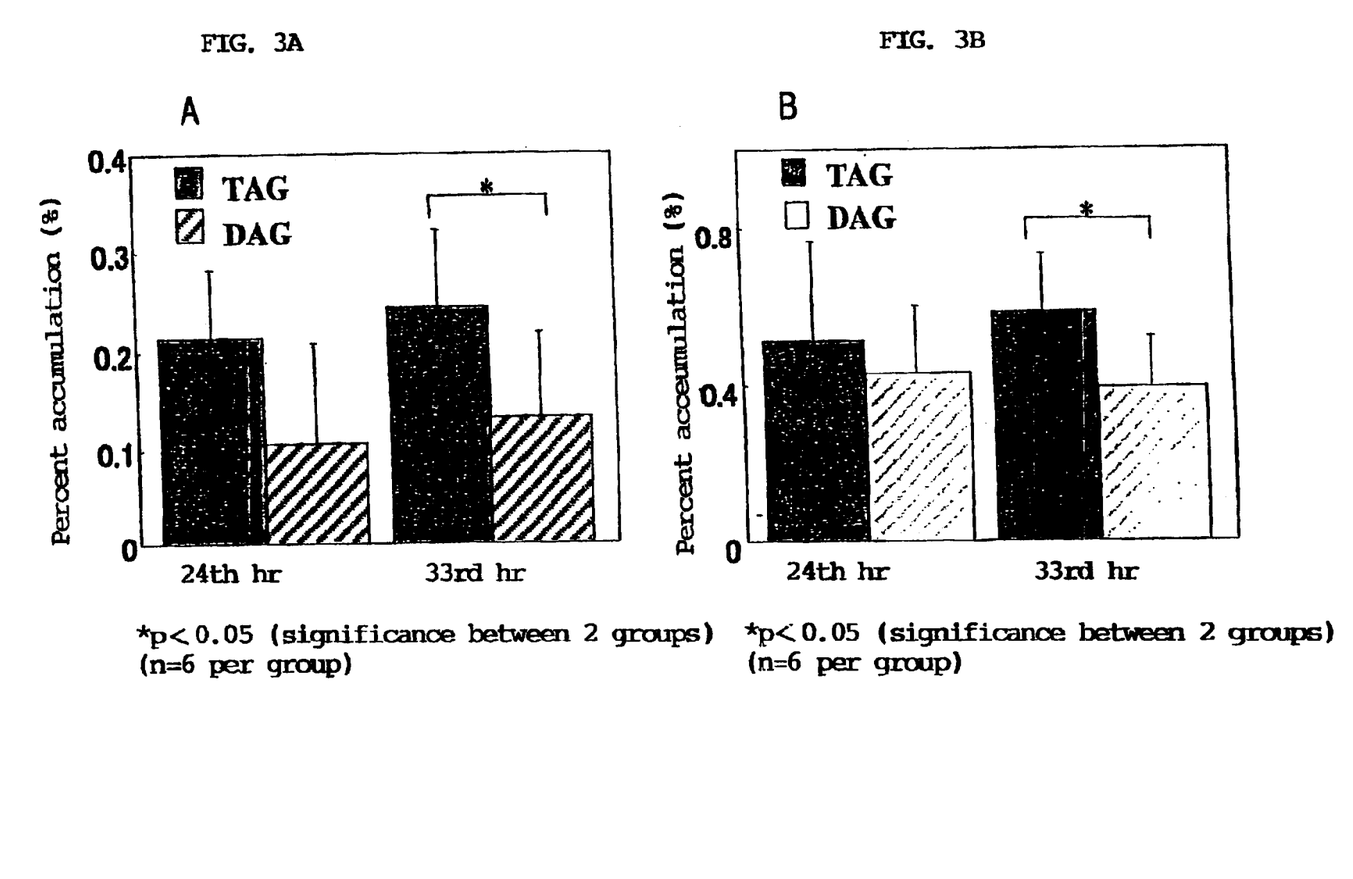
FIGS. 3A and 3B depict percent accumulations of epididymal fat and percent accumulations of mesenteric fat in mice which ingested diacylglycerols (DAG) and triacylglycerols (TAG), respectively.

In each of the DAG feed group and the TAG feed group, the percent accumulation of $^{13}C$ in fat was higher in the mesenteric fat (B) than in the epididymal fat (A). On the 33$^{rd}$ hour after the administration of the lipids, the percent accumulations of $^{13}C$ in both the epididymal fat and mesenteric fat were both found to be significantly low values in the DAG feed group than in the TAG feed group (FIG. 3).

From the foregoing, diacylglycerols have been found to be equipped with effect that, when ingested, they promote burning not only diacylglycerols but also other dietary lipids to excrete them as an expiration and hence; to suppress their accumulation as body fat.

Example 6

Remnant-Like Lipoprotein (RLP) Level Lowering Effect

The groups of volunteers relatively high in serum triacylglycerol level, each consisting of 8 adult male and female volunteers, used the above-described oil or fat compositions A to E, respectively, for one month (average ingestion: 10 g/day) in place of edible oils which they had used daily. Blood samples were drawn both before and after the use of the oil or fat compositions A to E, and their serum RLP levels were measured (Table 9).

The serum RLP levels were each quantitated based on the amount of cholesterol in a fraction which had been obtained by conducting fractionation with an anti-apo B-100-anti-apo Al monoclonal antibody affinity mixed gel.

TABLE 9

| Oil or fat composition | | c/(t + S) | RLP level |
| --- | --- | --- | --- |
| Invention | A | 20.1 | 83.1 |
| | B | 11.3 | 86.3 |
| | C | 6.2 | 92.1 |
| | D | NT | 90.3 |
| Comparative | Soybean oil | 5.1 | 103.8 |

Shown in terms of relative value when the initial values were supposed to be 100.
NT: Not tested.

As the ingestion of the diacylglycerol-containing oil or fat compositions A to E was able to lower the serum RLP levels, diacylglycerols can prevent diseases such as angina pectoris and myocardial infarction.

Example 7

Serum Leptin Lowering Effect

The groups of volunteers high in body mass index, each consisting of 5 male volunteers and 9 female volunteers, used the above-described oil or fat compositions A to D, respectively, for one month (average ingestion: 10 g/day) in place of edible oils which they had used daily. Blood samples were drawn both before and after the use of the oil or fat compositions A to D, and their serum leptin levels were measured (Table 10). The leptin levels were quantitated by the method which performs a measurement by using an antibody to human leptin [Clin. Chem., 42, 942 (1996)].

TABLE 10

| Oil or fat composition | | Relative serum leptin level |
| --- | --- | --- |
| Invention | A | 82.5 |
| | B | 85.2 |
| | C | 92.0 |
| | D | 90.1 |
| Comparative | Soybean oil | 105.8 |

Shown in terms of relative value when the serum leptin levels before the ingestion were supposed to be 100.

The volunteers who ingested the oil or fat composition A were found from CT scan images of their umbilical region that, as the serum leptin level lowered to 82.5% compared with the serum leptin level before the digestion (which was supposed to be 100), the subcutaneous fat area and visceral fat area dropped to 93.9% and 94.4%, respectively, and at the same time, the serum triacylglycerol level also dropped to 89.0%.

The oil or fat compositions A to D were all excellent in serum leptin level lowering effect.

Example 8

Blood Sugar Level Lowering Effect (1) Preparation of Diacylglycerol-Containing Oils/Fats
(1)-1

A high-DHA oil ("DHA-45", trade name; product of MARUHA CORPORATION) (200 parts by weight) and glycerol (10 parts by weight) were mixed. Subsequent to further mixing of an alkali catalyst (sodium methoxide, $CH_3ONa$) (0.6 part by weight), an a transesterification reaction was conducted under reduced pressure (0.133 kPa) at 100° C. for 4 hours. By chromatography on a silica gel column, fractionation of individual components was then conducted. Triacylglycerols (10.3 parts by weight), diacylglycerols (87.4 parts by weight), monoacylglycerols (1.9 parts by weight) and polymerized acylglycerol products (0.4 part by weight) were then mixed to prepare an oil or fat composition F.

(1)-2

Linseed oil ("SCAN-OIL", trade mark; importer: NIHON SHOJI K. K.) (180 parts by weight) and glycerol (12 parts by weight) were mixed. Following the procedure of the preparation (1)-1, a transesterification reaction and fractionation of individual components were conducted. Triacylglycerols (36.8 parts by weight), diacylglycerols (61.3 parts by weight), monoacylglycerols (0.5 part by weight), free fatty acids (0.8 part by weight) and polymerized acylglycerol products (0.6 part by weight) were then mixed to prepare an oil or fat composition G.

(1)-3

Perilla oil (140 parts by weight), olive oil (product of WAKO PURE CHEMICAL INDUSTRIES, LTD.) (70 parts by weight) and glycerol (20 parts by weight) were mixed. Following the procedure of the preparation (1)-1, a transesterification reaction and fractionation of individual components were conducted. A 100% monoacylglycerol fraction was provided as an oil or fat composition H.

Principal fatty acid compositions of monoacylglycerol and diacylglycerol fractions derived from the thus-obtained oil or fat compositions F, G and H are shown in Table 11.

TABLE 11

| | | Oil or fat composition | | |
|---|---|---|---|---|
| | | F | G | H |
| ω3 | C18:3 | 0 | 60.6 | 41.3 |
| | C20:5 | 6.7 | 0 | 0 |
| | C22:6 | 46.3 | 0 | 0 |
| Monoene | C16:1 | 3.4 | 0 | 0.2 |
| | C18:1 | 10.5 | 14.5 | 32.5 |
| | C20:1 | 1.4 | 0 | 0.4 |
| | C22:1 | 1.1 | 0 | 0 |
| ω6 | C18:2 | 1.3 | 15.4 | 12.9 |
| | C18:3 | 0.7 | 0 | 0 |
| Saturated | C14:0 | 2.2 | 0 | 0 |
| | C16:0 | 11.3 | 6.6 | 6.9 |
| | C14:0 | 2.7 | 2.9 | 2.2 |

Measured by gas chromatography after methylation.

Figure 4:
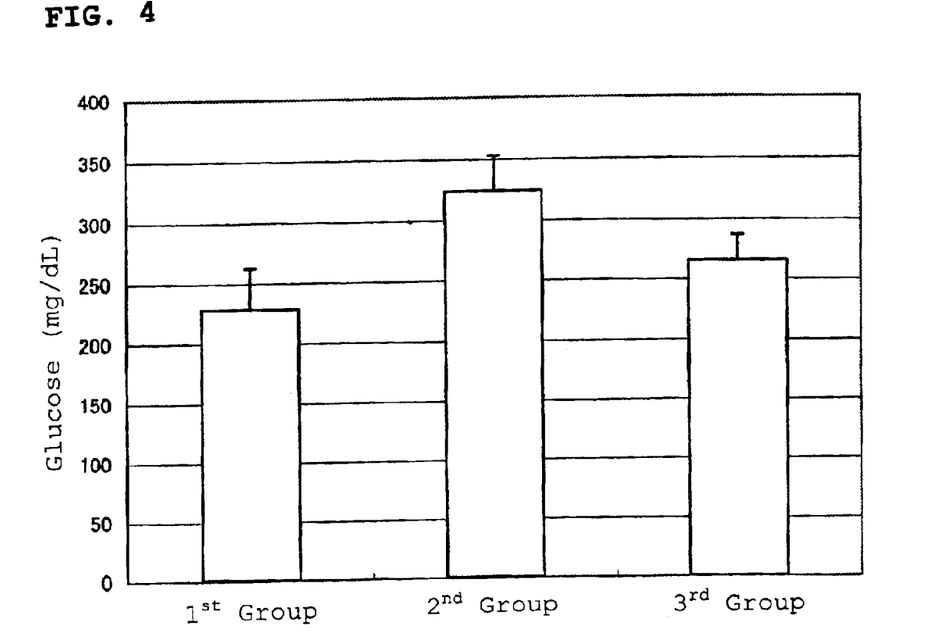
FIG. 4 is a diagram showing blood sugar level lowering effect of a diacylglycerol on diet-induced diabetes model C57BL/6J mice.

(2) Confirmation of Blood Sugar Level Lowering Effect by Using C57BL/6J Mice, Diet-Induced Diabetic Models C57BL/6J mice (male, 7 weeks old) were divided into three groups each of which consisted of 5 mice, and were reared with feeds of the corresponding compositions shown in Table 12. Thirty days later, blood samples were drawn from their abdominal aortas under etherization, and blood sugar levels were measured by "Glucose Test Wako" (trade name; product of WAKO PURE CHEMICAL INDUSTRIES, LTD.). The results are shown in FIG. 4.

TABLE 12

| | Group 1 | Group 2 | Group 3 |
|---|---|---|---|
| High-triacylglycerol oil[1] | 5.0% | 30.0% | 27.0% |
| Oil or fat composition F | — | — | 3.0% |
| Casein | 20.0% | 20.0% | 20.0% |
| Cellulose | 4.0% | 4.0% | 4.0% |
| Mineral mix | 3.5% | 3.5% | 3.5% |
| Vitamin mix | 1.0% | 1.0% | 1.0% |
| Potato starch | 66.5% | 41.5% | 41.5% |

[1]Refined soybean oil (product of The Nisshin Oil Mills, Ltd.; this will equally apply hereinafter).

In the group 2 (high lipid load feed (30% TG feed) group), significant rises in blood sugar level were observed compared with the group 1 (normal feed (5% TG feed) group). In the group 3 (the oil or fat composition F added group), on the other hand, rises in blood sugar level were lower compared with the group 1, and blood sugar levels were found to be lower than those in the group 2.

Figure 5:
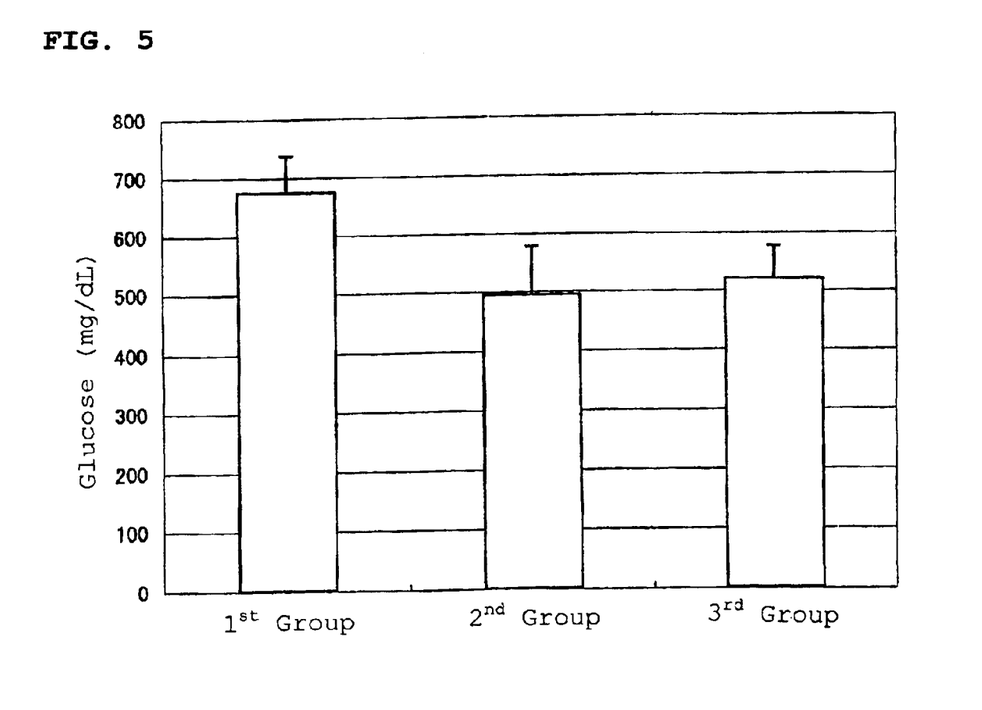
FIG. 5 is a diagram depicting blood sugar level lowering effect of a diacylglycerol on hereditary diabete model C57BL/KsJ-db/db mice.

(3) Confirmation of Blood Sugar Level Lowering Effect by Using C57BL/KsJ-db/db Mice, Hereditary Diabetic Models C57BL/KsJ-db/db mice (male, 7 weeks old) were divided into three groups each of which consisted of 10 mice, and were reared with feeds of the corresponding compositions shown in Table 13. Two months later, blood samples were drawn from their abdominal aortas under etherization, and blood sugar levels were measured by "Glucose Test Wako" (trade name; product of WAKO PURE CHEMICAL INDUSTRIES, LTD.). The results are shown in FIG. 5.

TABLE 13

| | Group 1 | Group 2 | Group 3 |
|---|---|---|---|
| High-triacylglycerol oil[1] | 10.0% | 7.0% | 6.0% |
| Oil or fat composition G | — | 3.0% | 3.0% |
| Oil or fat composition H | — | — | 1.0% |
| Casein | 20.0% | 20.0% | 20.0% |

TABLE 13-continued

| | Group 1 | Group 2 | Group 3 |
|---|---|---|---|
| Cellulose | 4.0% | 4.0% | 4.0% |
| Mineral mix | 3.5% | 3.5% | 3.5% |
| Vitamin mix | 1.0% | 1.0% | 1.0% |
| Potato starch | 61.5% | 61.5% | 61.5% |

[1]As defined in Table 12.

In the group 1 (normal feed (10% TG feed) group), a pronouncedly high blood sugar state was observed. In the groups 2 and 3 in which lipids were replaced by α-linolenic acid diacylglycerol (the oil composition G: 3%) or α-linolenic acid diacylglycerol/monoacylglycerol (the oil or fat composition G: 3%+oil or fat composition H: 1%), respectively, on the other hand, significant drops in blood sugar level were observed.

(4) Reduction in Human Blood Sugar Level

Three male volunteers (A, B, C) the fasting blood sugar levels of which were 120 mg/dL or higher were directed to ingest the oil or fat composition F, which was filled in soft capsules, in an amount of 2 g per day for 3 months without changing their diet life, and then, their blood sugar levels were measured by "Glucose Test Wako" (trade name; product of WAKO PURE CHEMICAL INDUSTRIES, LTD.). The results are shown in Table 14. As a result, reductions in blood sugar level were observed on all the volunteers.

TABLE 14

| | Initial level | 3 months later |
|---|---|---|
| Volunteer A, 39 years old | 123 | 101 |
| Volunteer B, 45 years old | 135 | 110 |
| Volunteer C, 42 years old | 142 | 103 |

(mg/dL)

Example 9

Insulin Resistance Improving Effect

Normal male volunteers of 24 or higher BMI (or body fat percentage: 23% or higher, slight obesity) were directed to orally ingest the oil or fat composition F, which had been formulated into capsules, at a dose of 2 g in a day. Blood insulin levels were measured both before and after the ingestion. As a result, the average of blood insulin levels pronouncedly dropped to 12.9 μU/mL after the completion of the ingestion (1 month) (p<0.05), although it was 16.3 μU/mL before the initiation of the digestion (initial level).

Example 10

Effects of Long-Term Digestion of Diacylglycerols on Serum Lipids in Type II Diabetes A. Testing Method (1) Test Oils Employed as test oils were an oil or fat composition I prepared in a similar manner as the oil or fat composition A by using rapeseed oil and a comparative oil or fat A (TAG) prepared with the same fatty acid composition as the oil or fat composition I by mixing rapeseed oil, soybean oil and sunflower oil. The fatty acid compositions of the employed oil or fat composition I and comparative oil or fat A are shown in Table 15. In the oil or fat composition I, the sum of 1,3-DAG and 1,2-DAG (2,3-DAG) accounted for 86%, and their ratio was 7:3. Besides these DAGS, triacylglycerols and monoacylglycerols (MAG) existed in proportions of 13% and 1%, respectively. Incidentally, the heat of combustion of the oil or fat composition I as measured by a bomb calorimeter was approximately 9 kcal/g (analyzed by Japan Food Research Laboratories, Tokyo, Japan).

TABLE 15

| Fatty acids | Oil or fat composition I | Comparative oil or fat A |
|---|---|---|
| C16 | 3.16 | 5.68 |
| C18 | 1.27 | 2.23 |
| C18:1 | 37.49 | 35.67 |
| C18:2 | 48.27 | 46.65 |
| C18:3 | 6.36 | 6.94 |
| Acylglycerol compositions | | |
| Triacylglycerols | 12.98 | 97.78 |
| Diacylglycerols | 85.89 | 1.43 |
| Monoacylglycerols | 1.06 | 0.00 |
| Free fatty acids | ND | ND |

ND: not detected (2) Volunteers and Meal

This study was conducted under full explanation and consent in compliance with the spirit of the Helsinki Declaration. Volunteers consisted of 24 day patients, who were aged from 38 to 79 and were under continued guidance on nutrition (dietotherapy) by Diabetic Outpatient Section, Internal Department, Itami City Hospital. Those diabetics were divided into two groups, one being the oil or fat composition I group which consisted of 11 diabetics (average age: 61.6±1.9 years old; 4 male diabetics and 7 female diabetics), and the other the comparative oil or fat A group which consisted of 13 diabetics (average age: 54.3±3.6 years old; 7 male diabetics and 6 female diabetics).

In the oil or fat composition I group and the comparative oil A group, the oil or fat composition I and the comparative oil or fat A were used as cooking oils, respectively, in place of oils employed daily. The volunteers were each directed to ingest the corresponding cooking oil with a daily target consumption of 10 g. In each of the groups, the period of study was set at 3 months from the initiation of use of the corresponding cooking oil, and tests were conducted by the double-blind method.

Concerning medication to the volunteers, the oil or fat composition I group consisted of 1 volunteer medicated using an insulin preparation and an HMG-CoA inhibitor in combination, 1 volunteer medicated with the insulin preparation, 4 volunteers medicated with a sulfonylurea preparation, 1 volunteer medicated using the sulfonylurea preparation and an α-glucosidase inhibitor in combination, 1 volunteer medicated with a biguanide preparation, 1 volunteer medicated using the biguanide preparation and the sulfonylurea preparation in combination, and 2 volunteers without any medication. The comparative oil or fat A group, on the other hand, consisted of 1 volunteer medicated with the HMG-CoA inhibitor, 3 volunteers medicated with the insulin preparation, 2 volunteers medicated with the sulfonylurea preparation, 1 volunteer medicated using the biguanide preparation and the sulfonylurea preparation in combination, 1 volunteer medicated with an EPA preparation, and 5 volunteers without any medication.

(3) Physical Measurements and Blood Tests

At intervals of 1 month after initiation of ingestion of the test oils, physical measurements and fasting blood sampling were conducted at the hospital. As physical measurement items, body weight, BMI, waist circumference and hip circumference were measured. As blood test items, on the other hand, triacylglycerols, total cholesterols (Chol), free fatty acids, LDL-Chol, HDL-Cho, remant-like lipoprotein (RLP)-Chol, lipoprotein (a) [Lp(a)], lipoprotein lipase (LPL) protein quantity, total ketone bodies, acetoacetic acid, 3-hydroxybutyric acid, PAI-1, leptin, insulin, glucose, hemoglobin A1c (HbA1c), apoproteins (ApoA-1, ApoB, ApoC-II, ApoC-III, ApoE), cholesterol ester transfer protein (CETP), and lecithin cholesterol acyltransferase (LCAT) were measured.

(4) Analysis of Serum Lipoproteins by HPLC

An analysis of serum lipoproteins was conducted in accordance with the method proposed by Usui et al. and making use of a gel filtration column (J. Lipid Res., 43(5), 805–814, 2002). This method has merits that the operation is simple and is practically unaffected by the composition and temperature of an eluent, reproducibility is very high, and serum can be accurately and quantitatively analyzed in a shorter time without needing it in a large amount.

Serum samples were each diluted with physiological saline, and reserved at 5° C. until its analysis for lipoproteins by HPLC.

(5) Statistical Testing Method

Each value so obtained was expressed in terms of mean±standard error (S.E.), while its variation from the corresponding initial value when the initial value was supposed to be 100% was expressed in terms of mean±standard error (S.E.). Inter-group comparisons were conducted by two-way ANOVA, and levels of significance were tested by Student's t-test. Further, comparisons between the initial value and values measured at intervals of 1 month after the initiation of ingestion of each test oil were conducted by Student's t-test to test the levels of significance.

Upon conducting two-way ANOVA, the intent-to-treat analysis was adopted for the data in the test period.

B. Results (1) Ingested Amounts of Test Oils and Physical Measurements

According to observations by attending physicians, neither deteriorations in physical conditions nor side effects by the ingestion of the test oil were acknowledged throughout the test period on all the volunteers in both the oil or fat composition I ingestion group and the comparative oil or fat A ingestion group. No changes were made to the medication and dosage during the test period. From the data of diet diaries, the amount of the test oil ingested per day was found to be 14.4±1.6 g in the oil or fat composition I group and 13.3±1.6 g in the comparative oil or fat A group. As a body weight change in the third month, a decrease of 0.4% (0.2 kg) was shown in the oil or fat composition I group, while an increase of 0.4% (0.3 kg) was shown in the comparative oil or fat A group. Concerning the changes in body weight over the three months, two-way ANOVA found no significant difference between both groups. In BMI and hipline, no difference was observed between both groups. As a waist circumference change in the third month, a decrease of 1.5% (1.5 cm) was shown in the oil or fat composition I group, while no change was shown in the comparative oil or fat A group. Concerning the change in body weight over the three months, two-way ANOVA found a significant difference (P=0.02) between both groups. Even on the volunteers the initial serum glucose levels of which were 110 mg/dL or higher, a significant difference (P<0.001) was observed in waist circumference between both groups.

(2) Blood Test

Among the serum test items, substantial changes were observed in triacylglycerols and HDL-Chol. As a result of two-way ANOVA of the changes over the three months, the oil or fat composition I group showed a lowering tendency in triacylglycerols and a significant increase (P<0.05) in HDL-Cho in comparison with the comparative oil or fat A group. Data of the volunteers the serum glucose levels of which were 110 mg/dL or higher were also analyzed. Concerning changes in glucose, triacylglycerols and plasma PAI-1 over the 3 months, significant differences were all observed by two-way ANOVA between both groups (they dropped in the oil or fat composition I group). As to serum ApoA-1 and ApoB over the three months, no changes were observed on all the volunteers and the volunteers, the serum glucose levels of which were 110 mg/dL or higher, in both groups. With respect to ApoC-II, ApoC-III and ApoE, on the other hand, lowering tendencies were shown in the oil or fat composition I group in comparison with the comparative oil or fat A group. Concerning serum free fatty acids, total ketone bodies, acetoacetic acid, 3-hydroxybutyric acid, NbAlc, insulin, total-Chol, LDL-Chol, RLP-Chol, LP(a), LPL proteins, leptin, CETP and LCAT, no significant differences were observed on all the volunteers and the volunteers, the serum glucose levels of which were 110 mg/dL or higher, in both groups.

(3) Analysis of Serum Lipoproteins by HPLC

Changes in TG and Chol levels in serum lipoprotein fractions obtained at intervals of 1 month after the initiation of the ingestion of the test oils are shown in Tables 16 and 17. Concerning the TG and Chol levels in CM (chylomicron) fractions, no changes were observed. As to the TG levels in VLDL fractions in the third month, the oil or fat composition I group indicated a decreasing tendency in comparison with the comparative oil or fat A group. Even on the volunteers the initial serum glucose levels of which were 110 mg/dL or higher, a significant difference (P=0.02) was observed in the change over the three months by two-way ANOVA between both groups. With respect to changes in the Chol levels in HDL fractions over the 3 months, all the volunteers and the volunteers, the serum glucose levels of which were 110 mg/dL or higher, showed increasing tendencies in the oil or fat composition group I, but no significant differences were observed between the oil or fat composition group I and the comparative oil or fat A group. Concerning changes over three months in the TG levels in LDL fractions and small dense LDL fractions obtained from all the volunteers, significant differences were observed by two-way ANOVA in both fractions between both groups. Even on the volunteers the serum glucose levels of which were 110 mg/dL or higher, the TG levels in the LDL fractions and small dense LDL fractions in the third month were observed to develop significant decreases (P<0.05) in the oil or fat composition I group in comparison with the comparative oil or fat A group.

TABLE 16

Changes in TG and Chol Levels in Serum Lipoprotein Fractions by HPLC method

| | Oil or fat composition I group (n = 11) | | | | Comparative oil or fat A group (n = 13) | | | | Two-way |
|---|---|---|---|---|---|---|---|---|---|
| | 0 month | 1 month | 2 months | 3 months | 0 month | 1 month | 2 months | 3 months | ANOVA |
| CM | | | | | | | | | |
| TG[a] % | 100 | 141.0 ± 48.2 | 515.6 ± 239.8 | 255.3 ± 105.6 | 100 | 123.0 ± 35.9 | 245.2 ± 58.5 | 480.8 ± 309.1 | |
| (mg/dL) | (0.77 ± 0.37) | (0.70 ± 0.30) | (0.82 ± 0.28) | (0.73 ± 0.43) | (0.47 ± 0.13) | (0.56 ± 0.27) | (0.76 ± 0.23) | (0.59 ± 0.16) | |
| Chol[b] % | 100 | 176.9 ± 72.6 | 716.5 ± 445.1 | 151.8 ± 63.8 | 100 | 105.3 ± 35.7 | 378.7 ± 182.1 | 178.9 ± 63.7 | |
| (mg/dL) | (0.27 ± 0.15) | (0.32 ± 0.17) | (0.37 ± 0.17) | (0.30 ± 0.16) | (0.13 ± 0.04) | (0.19 ± 0.08) | (0.23 ± 0.06) | (0.16 ± 0.04) | |
| VLDL | | | | | | | | | |
| TG % | 100 | 123.9 ± 16.0 | 121.1 ± 17.9 | 94.5 ± 8.8 | 100 | 117.7 ± 8.9 | 123.9 ± 17.3 | 130.1 ± 15.3 | |
| (mg/dL) | (115.8 ± 28.2) | (127.5 ± 25.4) | (111.2 ± 21.6) | (100.1 ± 23.8) | (85.6 ± 21.0) | (117.7 ± 36.8) | (92.2 ± 19.9) | (98.1 ± 19.0) | |
| Chol % | 100 | 120.6 ± 10.6 | 123.4 ± 7.8 | 102.5 ± 6.9 | 100 | 137.0 ± 9.8 | 123.7 ± 6.8 | 107.2 ± 8.8 | |
| (mg/dL) | (50.0 ± 5.1) | (58.0 ± 5.2) | (58.8 ± 4.1) | (51.0 ± 6.1) | (41.2 ± 2.5) | (55.2 ± 3.9) | (49.9 ± 3.0) | (43.7 ± 4.5) | |
| LDL | | | | | | | | | |
| TG % | 100 | 91.4 ± 5.3 | 58.7 ± 5.1[###] | 84.1 ± 7.1[#] | 100 | 76.5 ± 6.2 | 93.5 ± 18.8 | 111.4 ± 10.8 | Interaction (P = 0.03) |
| (mg/dL) | (85.3 ± 11.4) | (76.7 ± 10.8) | (47.8 ± 6.9) | (67.7 ± 8.6) | (60.5 ± 9.5) | (43.8 ± 7.4) | (43.8 ± 4.5) | (60.2 ± 7.0) | |
| Chol % | 100 | 95.8 ± 4.8 | 92.7 ± 5.6 | 111.6 ± 7.2 | 100 | 85.8 ± 5.0 | 104.8 ± 9.0 | 114.8 ± 8.6 | |
| (mg/dL) | (114.3 ± 9.5) | (108.0 ± 9.4) | (103.5 ± 8.6) | (125.8 ± 11.8) | (106.8 ± 8.0) | (88.7 ± 6.3) | (106.6 ± 8.4) | (118.4 ± 8.8) | |

[a]TG: Triacylglycerol
[b]Chol: Cholesterol
Values are mean ± S.E.
Parenthesized values are actual measurements.
[#],[###]P < 0.05, P < 0.001 vs the initial value (0 month).

TABLE 17

Changes in TG and Chol Levels in Serum Lipoprotein Fractions by HPLC method

| | Oil or fat composition I group (n = 11) | | | | Comparative oil or fat A group (n = 13) | | | | Two-way |
|---|---|---|---|---|---|---|---|---|---|
| | 0 month | 1 month | 2 months | 3 months | 0 month | 1 month | 2 months | 3 months | ANOVA |
| HDL | | | | | | | | | |
| TG[a] % | 100 | 108.3 ± 7.4 | 92.3 ± 8.0 | 100.4 ± 10.7 | 100 | 103.1 ± 7.9 | 105.8 ± 6.7 | 106.9 ± 7.6 | |
| (mg/dL) | (25.0 ± 4.0) | (26.2 ± 3.8) | (21.6 ± 3.7) | (22.5 ± 2.7) | (21.3 ± 1.8) | (22.7 ± 3.5) | (21.8 ± 1.7) | (21.8 ± 1.6) | |
| Chol[b] % | 100 | 102.1 ± 4.1 | 105.1 ± 5.2 | 116.6 ± 5.1[##] | 100 | 104.4 ± 4.1 | 112.1 ± 3.9 | 112.6 ± 5.6 | |
| (mg/dL) | (39.0 ± 1.5) | (39.7 ± 2.1) | (40.7 ± 2.2) | (45.5 ± 2.8) | (44.8 ± 2.7) | (46.7 ± 3.4) | (49.5 ± 2.6) | (50.2 ± 3.6) | |
| Small dense LDL | | | | | | | | | |
| TG % | 100 | 97.1 ± 6.3 | 65.8 ± 6.1[###] | 80.6 ± 7.9[#],* | 100 | 83.2 ± 8.0 | 94.6 ± 16.6 | 106.6 ± 8.9 | Interaction (P = 0.046) |
| (mg/dL) | (21.9 ± 3.4) | (20.4 ± 3.0) | (13.8 ± 2.4) | (16.5 ± 2.6) | (15.0 ± 2.3) | (12.6 ± 2.8) | (11.8 ± 1.4) | (14.6 ± 1.8) | |
| Chol % | 100 | 96.4 ± 4.5 | 108.1 ± 3.6 | 117.4 ± 7.4 | 100 | 83.2 ± 5.1 | 113.8 ± 11.8 | 125.8 ± 9.4 | |
| (mg/dL) | (32.4 ± 2.7) | (30.7 ± 2.4) | (35.2 ± 3.4) | (38.2 ± 4.6) | (30.1 ± 2.4) | (24.3 ± 1.8) | (33.1 ± 3.5) | (37.5 ± 3.9) | |

[a]TG: Triacylglycerol
[b]Chol: Cholesterol
Values are mean ± S.E.
Parenthesized values are actual measurements.
[#],[##],[###] $P < 0.05$, $P < 0.01$, $P < 0.001$ vs the initial value (0 month).
*$P < 0.05$ vs the comparative oil or fat A group (4) Evaluation of HOMA-R Values Values of HOMA-R, an index of insulin resistance, were evaluated. HOMA-R (homeostasis model assessment insulin resistance index) is calculated by: Starving sugar blood level (mg/dL)×Starving insulin level ($\mu$U/mL)÷405. HOMA-R is an index of insulin resistance, and its normal value is smaller than 2. A value of 4 or greater is interpreted to indicate a high degree of insulin resistance. As a result, HOMA-R increased by 39% 3 months later in the comparative oil or fat A group, while HOMA-R decreased by 19% in the oil or fat composition I group.

As demonstrated above, it has been found that by administration of an effective amount of a diacylglycerol to a diabetic patient, insulin resistance improving effect, HOMA-R lowering effect, lipid metabolism improving effect, and improving effects for the triacylglycerol level and/or cholesterol level in serum lipoprotein fraction are exhibited to make improvements in various diabetes-associated symptoms.

It has also become evident that dietary therapy in which a diacylglycerol is administered in an effective amount is effective for diabetics. This indicates that diacylglycerol-containing medical foods for diabetic patients are useful.

Example 11

Effects of Long-Term Digestion of Diacylglycerols on Glycohemoglobin A1c (HbA1c) in Type II Diabetics (1) Test Oils Similarly to Example 10, the oil or fat composition I and the comparative oil or fat A (TAG) were used.

(2) Volunteers and Meal

This study was conducted under full explanation and consent in compliance with the spirit of the Helsinki Declaration. Selected as volunteers were 16 day patients, who were under continued guidance on nutrition (dietary therapy) by Diabetic Outpatient Section, Internal Department, Itami City Hospital. Those diabetics were divided into two groups, one being the oil or fat-composition I group which consisted of 8 diabetics (average age: 56.8±17.3 years old; 3 male diabetics and 5 female diabetics), and the other the comparative oil or fat A group which consisted of 8 diabetics (average age: 54.1±18.8 years old; 4 male diabetics and 4 female diabetics).

As in Example 10, the oil or fat composition I and the comparative oil or fat A were used as cooking oils, respectively, in place of cooking oils employed daily. The volunteers were each directed to ingest the corresponding cooking oil with a daily target consumption of 10 g. In each of the groups, the period of study was set at 3 months from the initiation of use of the corresponding cooking oil, and tests were conducted by the double-blind method.

Concerning medication to the volunteers, the oil or fat composition I group consisted of 1 volunteer medicated with the insulin preparation, 1 volunteer medicated with the sulfonylurea preparation, 1 volunteer medicated with the $\alpha$-glucosidase inhibitor, and 2 volunteers without any medication. The comparative oil or fat A group, on the other hand, consisted of 1 volunteer medicated with the sulfonylurea preparation, 1 volunteer medicated with the $\alpha$-glucosidase inhibitor, and 6 volunteers without any medication.

(3) Evaluation of HbA1c

At intervals of 1 month after the initiation of the ingestion of the test oils, physical measurements and fasting blood sampling were conducted at the hospital. Values of blood HbA1c, one of principal diabetes markers, were measured by HPLC method (Clin. Chem., 30, 1746, 1984).

As a result, the HbA1c value (%, mean±S.D.) significantly dropped from 6.41±1.15 (upon initiation of the test) to 5.79±0.85 (3 months after) in the oil or fat composition I group. This value (3 months after) falls within the normal value range (4.3 to 5.8%) specified by Japan Diabetes Society (J. Japan Diab. Soc., 37, 855, 1994). In the comparative oil or fat A group, on the other hand, the HbA1c value was 6.88±0.53 (upon initiation of the test) and 6.65±0.73 (3 months after), and did not change substantially.

As demonstrated above, it has become evident that the HbAlc value is improved by ingesting the oil or fat composition I according to the present invention.

What is claimed is:

1. A method for improving insulin resistance in a diabetic, which comprises administering an effective amount of a diacylglycerol to said diabetic patient.

2. The method according to claim 1, wherein 15 to 90 wt. % of constituent fatty acids of said diacylglycerol comprise ω3 unsaturated fatty acids.

3. The method according to claim 1 or 2, wherein 1,3-diacylglycerols in said diacylglycerol amount to at least 50 wt. % of the whole diacylglycerol.

* * * * *